(12) United States Patent
Kappler et al.

(10) Patent No.: US 11,226,298 B2
(45) Date of Patent: Jan. 18, 2022

(54) X-RAY IMAGING SYSTEM AND METHOD OF X-RAY IMAGING

(71) Applicant: Siemens Healthcare GmbH, Erlangen (DE)

(72) Inventors: Steffen Kappler, Effeltrich (DE);
Marcus Radicke, Veitsbronn (DE);
Jörg Freudenberger, Kalchreuth (DE);
Anja Fritzler, Erlangen (DE); Peter Geithner, Erlangen (DE); Peter Hackenschmied, Nuremberg (DE);
Thomas Weber, Hausen (DE)

(73) Assignee: Siemens Healthcare GmbH, Erlangen (DE)

( * ) Notice: Subject to any disclaimer, the term of this patent is extended or adjusted under 35 U.S.C. 154(b) by 108 days.

(21) Appl. No.: 16/586,386

(22) Filed: Sep. 27, 2019

(65) Prior Publication Data

US 2020/0182806 A1  Jun. 11, 2020

Related U.S. Application Data

(60) Provisional application No. 62/776,915, filed on Dec. 7, 2018.

(30) Foreign Application Priority Data

Sep. 6, 2019 (EP) .................................. 19195778

(51) Int. Cl.
*G01N 23/20* (2018.01)
*G01N 23/04* (2018.01)
(Continued)

(52) U.S. Cl.
CPC ..... *G01N 23/20083* (2013.01); *A61B 6/4266* (2013.01); *G01N 23/04* (2013.01);
(Continued)

(58) Field of Classification Search
CPC ............ G01N 2223/507; G01N 23/04; G01N 23/20008; G01N 23/2206;
(Continued)

(56) References Cited

U.S. PATENT DOCUMENTS 4,382,181 A    5/1983  Wang
4,850,002 A *  7/1989  Harding ................. A61B 6/483
                                                    378/87
(Continued)

FOREIGN PATENT DOCUMENTS

WO   WO2010120377 A2   10/2010
WO   WO2015200551 A1   12/2015

OTHER PUBLICATIONS

European Search Report for European Application No. 19195778.6-1001 dated Apr. 6, 2020.

*Primary Examiner* — Chih-Cheng Kao
(74) *Attorney, Agent, or Firm* — Lempia Summerfield Katz LLC

(57) ABSTRACT

An x-ray imaging system includes an x-ray source configured to emit x-ray radiation towards a sample, and a primary detector configured to detect x-ray radiation from the x-ray source passing through the sample. The x-ray imaging system also includes a secondary detector configured to detect x-ray radiation from the x-ray source scattered in the sample, and imaging optics configured to guide x-ray radiation scattered in the sample onto the secondary detector.

11 Claims, 3 Drawing Sheets

(51) Int. Cl.
*G01N 23/20008* (2018.01)
*A61B 6/00* (2006.01)

(52) U.S. Cl.
CPC ...... *G01N 23/20008* (2013.01); *A61B 6/4241* (2013.01); *A61B 6/483* (2013.01); *A61B 6/502* (2013.01); *A61B 6/5282* (2013.01); *G01N 2223/045* (2013.01)

(58) Field of Classification Search
CPC ........ G01N 2223/045; G01N 23/20083; A61B 6/4241; A61B 6/4266; A61B 6/502; A61B 6/5282
See application file for complete search history.

(56) References Cited

U.S. PATENT DOCUMENTS

| | | | |
|---|---|---|---|
| 6,175,117 B1 * | 1/2001 | Komardin | A61B 6/483 378/88 |
| 8,331,534 B2 | 12/2012 | Silver | |
| 9,066,702 B2 | 6/2015 | Silver | |
| 9,326,744 B2 | 5/2016 | Silver | |
| 2004/0184574 A1 * | 9/2004 | Wu | A61B 6/563 378/5 |
| 2006/0140340 A1 | 6/2006 | Kravis | |
| 2007/0172022 A1 * | 7/2007 | Schlomka | A61B 6/483 378/6 |
| 2008/0205598 A1 * | 8/2008 | Van Stevendaal | A61B 6/5235 378/88 |
| 2011/0038455 A1 | 2/2011 | Silver | |
| 2013/0010927 A1 * | 1/2013 | Seppi | A61B 6/032 378/86 |
| 2013/0188773 A1 | 7/2013 | Silver | |
| 2015/0003581 A1 | 1/2015 | Silver | |
| 2015/0369758 A1 | 12/2015 | Silver | |
| 2016/0242713 A1 | 8/2016 | Silver | |
| 2017/0219501 A1 * | 8/2017 | Yakimov | G01N 23/203 |
| 2018/0038988 A1 * | 2/2018 | Morton | G01N 23/203 |
| 2018/0235562 A1 * | 8/2018 | Petschke | A61B 6/032 |
| 2018/0284036 A1 | 10/2018 | Silver | |

* cited by examiner

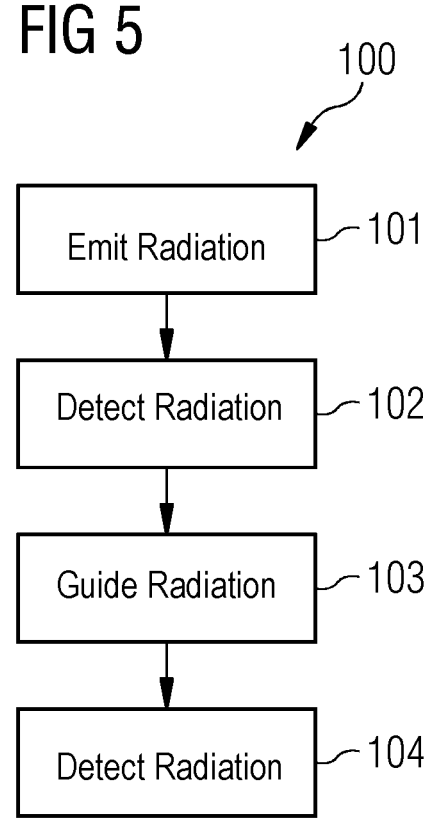

X-RAY IMAGING SYSTEM AND METHOD OF X-RAY IMAGING

This application claims the benefit of U.S. provisional patent application No. 62/776,915, filed on Dec. 7, 2018, and EP 19195778.6, filed on Sep. 6, 2019, which are hereby incorporated by reference in their entirety.

BACKGROUND

The present embodiments are directed to an x-ray imaging system and a method of x-ray imaging.

X-ray radiation is being used in a number of applications, ranging from medical imaging or therapy, security checks at airports, to crystallography. The most common method of x-ray imaging includes measuring the absorption of x-ray radiation passing through a sample on the way from an x-ray source to a detector. In that way, a two-dimensional transmission x-ray image of the sample may be obtained For example, for medical imaging, obtaining a three-dimensional image of the internal structure of the examined sample is often desirable. Commonly used methods for examining the three-dimensional structure of a sample include, for example, taking several transmission images with either different viewing angles or shifted focal planes. Each procedure of taking a transmission image exposes the sample to x-ray radiation. As in medical imaging, the sample to be examined often includes a living patient, and the dose of x-ray radiation to which the patient is exposed should be kept to a minimum for safety reasons.

SUMMARY AND DESCRIPTION

The scope of the present invention is defined solely by the appended claims and is not affected to any degree by the statements within this summary.

The present embodiments may obviate one or more of the drawbacks or limitations in the related art. For example, performing three-dimensional (3D) x-ray imaging is simplified.

An x-ray imaging system includes an x-ray source configured to emit x-ray radiation towards a sample, and a primary detector configured to detect x-ray radiation from the x-ray source passing through the sample. The x-ray imaging system also includes a secondary detector configured to detect x-ray radiation from the x-ray source scattered in the sample, and imaging optics configured to guide x-ray radiation scattered in the sample onto the secondary detector.

A method of x-ray imaging is also provided. In the method, x-ray radiation is emitted from an x-ray source towards a sample. X-ray radiation from the x-ray source passing through the sample is detected with a primary detector. X-ray radiation from the x-ray source scattered in the sample is detected with a secondary detector. The x-ray radiation scattered in the sample is guided onto the secondary detector with imaging optics.

Transmission x-ray imaging is combined with detecting scattered x-ray radiation. The scattered x-ray radiation may be used to create x-ray images from different viewing angles simultaneously with the primary transmission x-ray image. This allows obtaining information about the internal, three-dimensional structure of a sample without a need to prolong the process of imaging. This thus allows three-dimensional imaging with advantageously lower radiation doses of two-dimensional imaging.

According to an embodiment, the x-ray source is configured to emit x-ray radiation in the form of a fan beam. In this configuration, the origin of the scattered x-ray radiation detected by the secondary detector may be determined in three-dimensional space, allowing for advantageously improved information about the internal structure of the sample.

According to a further embodiment, the x-ray source is configured to emit monochromatic x-ray radiation. This configuration allows for x-ray imaging with advantageously reduced radiation dosages.

According to a further embodiment, the primary detector is configured to determine the energy of detected x-ray photons. This configuration allows the primary detector to differentiate between scattered and non-scattered photons, advantageously providing further information concerning the internal structure of the sample.

According to a further embodiment, the secondary detector is configured to determine the energy of detected x-ray photons. This configuration allows the secondary detector to determine the scattering processes inside the sample, advantageously providing further information concerning the internal structure of the sample.

According to a further embodiment, the x-ray imaging system includes a plurality of secondary detectors. This allows taking multiple secondary x-ray images simultaneously, enabling advantageously accelerated x-ray imaging.

According to a further embodiment, the x-ray imaging system is configured to be movable around the sample. This allows subsequently taking multiple x-ray images, enabling the system to advantageously generate more data concerning the internal structure of the sample.

According to an embodiment of the method, x-ray radiation emitted by the x-ray source is emitted in the form of a fan beam passing through the sample. In this configuration, the origin of the scattered x-ray radiation detected by the secondary detector may be determined in three-dimensional space, allowing for advantageously improved information about the internal structure of the sample.

According to a further embodiment of the method, the x-ray radiation emitted by the x-ray source is emitted as monochromatic x-ray radiation. Photons detected by the primary detector that have lower energy than the monochromatic x-ray radiation emitted by the x-ray source are ignored for x-ray imaging. This improves the signal-to-noise ratio of the transmission x-ray image created by the primary detector.

According to a further embodiment of the method, information relating to the photons detected by the primary detector that have lower energy than the monochromatic x-ray radiation emitted by the x-ray source is used for improving the x-ray imaging. This allows for correcting algorithms to be created concerning both elastic and non-elastic scattering inside the sample.

According to a further embodiment of the method, intensity of the x-ray radiation detected by the secondary detector is used to analyze the sample. This allows for determining the distribution of different materials inside the sample.

According to a further embodiment of the method, the x-ray radiation emitted by the x-ray source is emitted as monochromatic x-ray radiation. Photons detected by the secondary detector that have lower energy than the monochromatic x-ray radiation emitted by the x-ray source are used to analyze the sample. This configuration allows the secondary detector to determine the scattering processes inside the sample, advantageously providing further information concerning the internal structure of the sample.

The above-mentioned configurations and further embodiments may be combined with each other, if reasonable. Further possible configurations, further embodiments, and further implementations also include combinations of features described above or in the following with regard to the examples of implementation not explicitly mentioned. For example, the person of ordinary skill in the art will also add individual aspects as improvements or additions to the respective fundamental form of the present invention.

BRIEF DESCRIPTION OF THE DRAWINGS

FIG. 5 is a schematic flow chart of an embodiment of a method of x-ray imaging.

DETAILED DESCRIPTION

The following figures are intended to convey a further understanding of the forms in which the present embodiments are carried out. The figures illustrate embodiments and serve in connection with the description to explain principles and concepts of the present embodiments. Other embodiments and many of the above-mentioned advantages may be derived from the drawings. The elements of the drawings are not necessarily shown to scale.

In the figures of the drawings, same elements, characteristics, and components with the same function and effect are provided with the same reference signs, unless otherwise specified.

Figure 1:
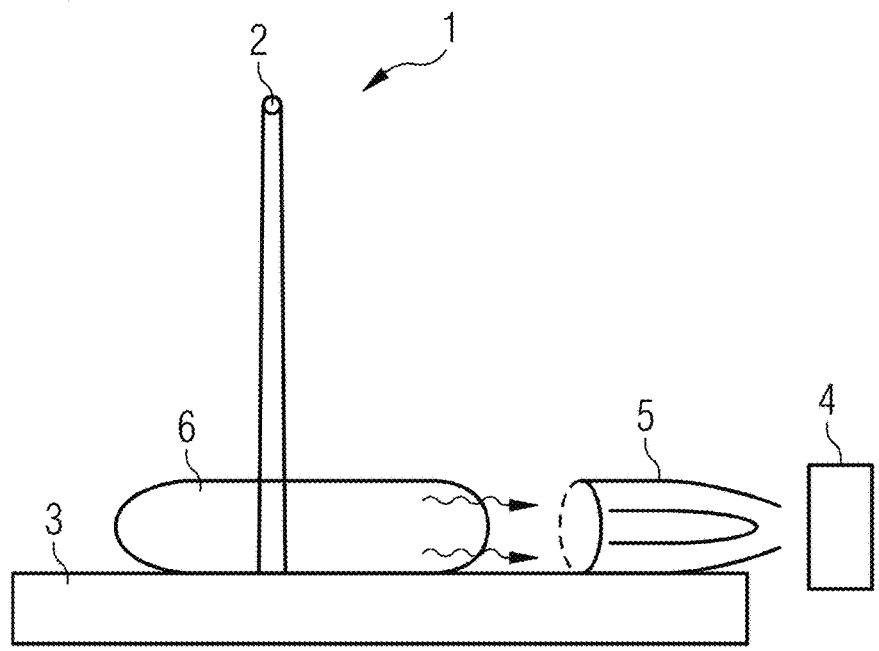
FIG. 1 is a schematic representation of an embodiment of an x-ray imaging system.

FIG. 1 shows a schematic representation of an embodiment of an x-ray imaging system 1. The x-ray imaging system 1 includes an x-ray source 2, a primary detector 3, a secondary detector 4, and imaging optics 5. A sample 6 is arranged between the x-ray source 2 and the primary detector 3. The secondary detector 4 is arranged off to a side from the x-ray source 2 and the primary detector 3. The imaging optics 5 is arranged between the sample 6 and the secondary detector 4.

In use, the x-ray source 2 emits x-ray radiation towards the sample 6. Part of the x-ray radiation emitted by the x-ray source 2 passes through the sample 6 without being absorbed or scattered and reaches the primary detector 3. The x-ray radiation detected by the primary detector 3 may then be used to construct a two-dimensional transmission x-ray image.

A part of the x-ray radiation emitted by the x-ray source 2 is scattered in the sample 6. Some of that scattered x-ray radiation is scattered in the direction of the secondary detector 4. The imaging optics 5 guides that scattered x-ray radiation onto the secondary detector 4. The x-ray radiation detected by the secondary detector 4 may then be used to construct a side-view image of the sample 6.

The x-ray radiation emitted by the x-ray source 2 may be emitted in the form of a fan beam. By passing the fan beam through the sample, the transmission x-ray image may be constructed one line at a time from the x-ray radiation detected by the primary detector 3. At the same time, for each line in the transmission image, a corresponding side view image may be constructed from the x-ray radiation detected by the secondary detector 4. These multiple side view images may then be combined to recreate the internal three-dimensional structure of the sample.

In FIG. 1, the imaging optics 5 is shown as including polycapillary optics. This is merely an exemplary embodiment of imaging optics used with x-ray radiation. Other embodiments may include zone plates, compound refractive lenses, reflection optics, and other kinds of imaging optics.

Figure 2:
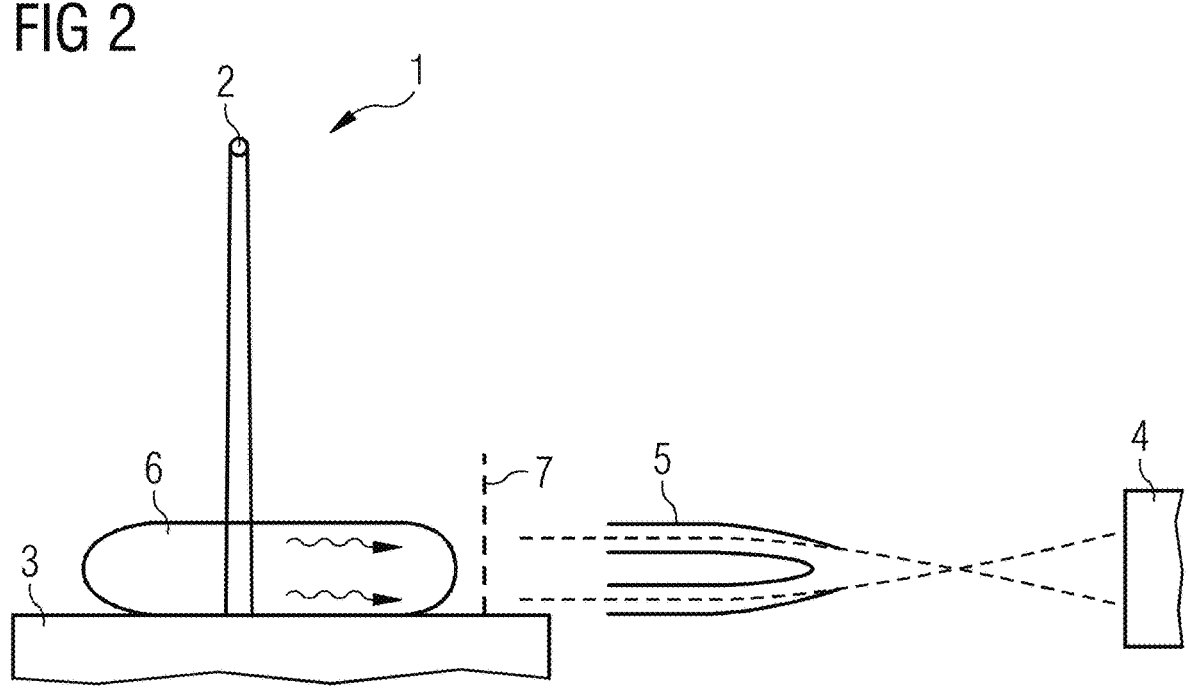
FIG. 2 is a schematic representation of a further embodiment of an x-ray imaging system.

FIG. 2 shows a schematic representation of a further embodiment of an x-ray imaging system 1. The embodiment shown in FIG. 2 includes essentially the same features as the embodiment shown in FIG. 1. In addition, the x-ray imaging system 1 shown in FIG. 2 includes a collimator 7 arranged between the sample 6 and the imaging optics 5.

The collimator 7 narrows the scattered x-ray radiation traveling towards the imaging optics 5 and provides that only x-ray radiation scattered in a direction perpendicular to the x-ray radiation emitted by the x-ray source 2 reaches the imaging optics 5 and subsequently the secondary detector 4. In this way, the image quality of the side view image created from the x-ray radiation detected by the secondary detector 4 may be advantageously improved.

Figure 3:
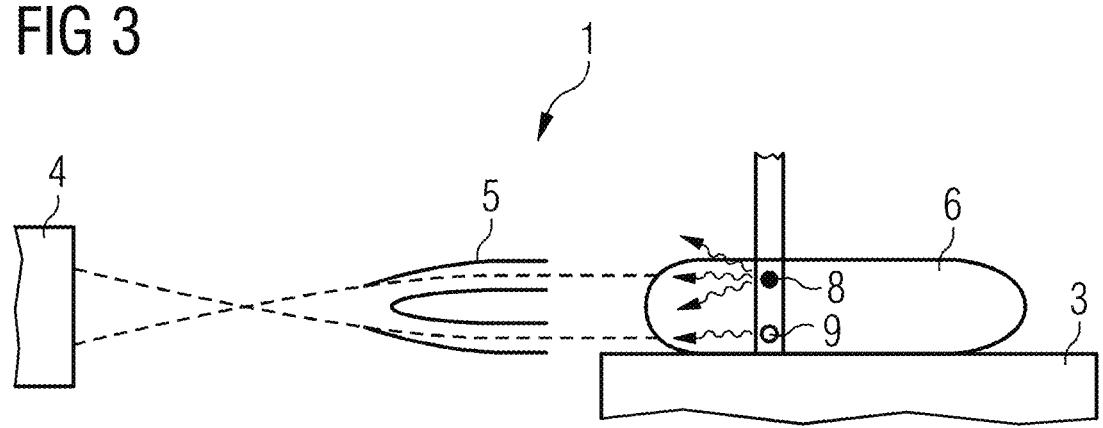
FIG. 3 is a schematic representation of an application of a further embodiment of an x-ray imaging system.

FIG. 3 shows a schematic representation of a further embodiment of an x-ray imaging system 1. FIG. 3 shows a primary detector 3, a secondary detector 4, imaging optics 5, and a sample 6, which are essentially the same as shown in FIG. 1. Additionally, FIG. 3 shows a foreign object 8 located inside the sample 6, as well as a corresponding volume 9 inside the sample of the same size as the foreign object 8.

When x-ray radiation coming from an x-ray source passes through the sample 6, both the foreign object 8, as well as the corresponding volume 9, scatter part of the x-ray radiation towards the imaging optics 5 and secondary detector 4. As shown in FIG. 3, the foreign object 8 may scatter more x-ray radiation than the corresponding volume 9. Consequently, the secondary detector 4 detects x-ray radiation of higher intensity at a point where x-ray radiation scattered by the foreign object has been guided by the imaging optics 5, when compared to the points on the secondary detector 4, where x-ray radiation scattered by the corresponding volume 9 has been guided by the imaging optics 5.

This difference in intensity may then be used to obtain information concerning the properties of the foreign object 8. For example, in human breast tissue, such a foreign object may include a microcalcification (e.g., tricalcium phosphate). Such a microcalcification scatters x-ray radiation at a rate of about 1.5 times as the corresponding volume of water. Consequently, if the x-ray radiation scattered by the foreign body 8 is about 1.5 times as high as the intensity of the x-ray radiation scattered by the corresponding volume 9, this indicates that the foreign body includes such a microcalcifiaction.

In addition or alternatively, the x-ray radiation coming from the x-ray source may include monochromatic x-ray radiation. Scattered x-ray radiation may have a lower energy of incoming x-ray radiation if the scattering process is inelastic (e.g., if x-ray radiation is scattered by the Compton Effect).

When the secondary detector is configured to determine the energy of the detected x-ray radiation and when the incoming x-ray radiation is monochromatic (e.g., monoenergetic), the difference in energy between incoming and scattered x-ray radiation may easily be determined. From that difference, further information concerning the scattering processes and consequently the material distribution inside the sample may be gained.

When the primary detector is configured to determine the energy of the detected x-ray radiation and when the incoming x-ray radiation is monochromatic (e.g., monoenergetic), it is possible to determine which photons arriving at the primary detector have passed through the sample and which photons have been scattered in an inelastic matter simply by filtering by the energy level of the detected x-ray photons. The photons that had been scattered may then be ignored for the creation of the transmission x-ray image, which improves the signal-to-noise ratio of the x-ray image. Additionally or alternatively, the scattered x-ray photons detected by the primary detector may be used to construct a scatter image. Such a scatter image may be further used to create correction algorithms that may improve the quality of the x-ray image by providing information concerning not only inelastic scattering but also estimations concerning elastic scattering processes, like Thomson- and/or Rayleigh scattering.

Figure 4:
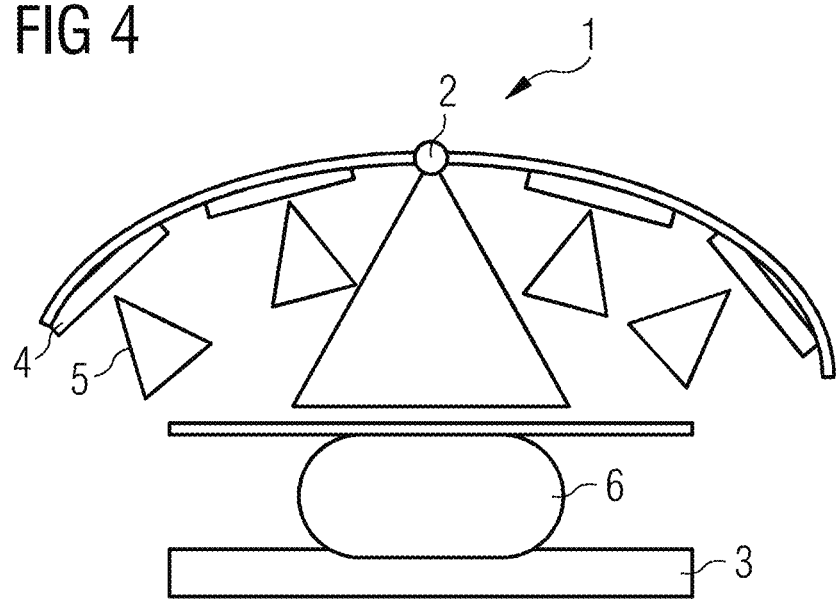
FIG. 4 is a schematic representation of a further embodiment of an x-ray imaging system.

FIG. 4 shows a schematic representation of a further embodiment of an x-ray imaging system 1. The x-ray imaging system 1 shown in FIG. 4 includes an x-ray source 2, a primary detector 3, a plurality of secondary detectors 4, and corresponding imaging optics 5. A sample 6 is arranged between the x-ray source 2 and the primary detector 3. The plurality of secondary detectors 4 are arranged on a circular arc opposite to the primary detector 3 from the sample 6. The plurality of imaging optics 5 are arranged between the sample 6 and the respective secondary detectors 4.

In application, the x-ray imaging system 1 functions essentially the same as described in conjuncture with FIG. 1. Instead of using scattered x-ray radiation detected by a singular secondary detector 4 to create a side-view image of the sample, in the embodiment shown in FIG. 4, scattered x-ray radiation detected by the plurality of secondary detectors 4 may be used to create a plurality of images of the sample 6 from different viewing angles. This plurality of images contains additional information about the internal structure of the sample.

The primary detector 3 and the plurality of secondary detectors 4 may remain stationary in order to perform a sort of non-mechanical tomosynthesis. Alternatively, the primary detector 3 and the plurality of secondary detectors 4 may be rotated around the sample.

FIG. 5 shows a schematic flow chart of a method 100 of x-ray imaging. In a first method act 101, x-ray radiation is emitted from an x-ray source towards a sample. In a further method act 102, x-ray radiation from the x-ray source passing through the sample is detected with a primary detector.

In a further method act 103, x-ray radiation scattered in the sample is guided onto a secondary detector with imaging optics. In a further method act 104, the x-ray radiation from the x-ray source scattered in the sample is detected with the secondary detector.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An X-ray imaging system comprising:
   an x-ray source configured to emit x-ray radiation towards a sample;
   a primary detector positioned opposite the x-ray source, such that the x-ray source and the primary detector are disposed on opposite sides of the sample, respectively, when the x-ray radiation is emitted towards the sample, the primary detector being configured to detect x-ray radiation from the x-ray source passing through the sample;
   at least one secondary detector configured to detect x-ray radiation from the x-ray source scattered in the sample; and
   imaging optics disposed between the at least one secondary detector and the sample when the x-ray radiation is emitted towards the sample, the imaging optics being configured to guide x-ray radiation scattered in the sample onto the at least one secondary detector; and
   a collimator disposed between the imaging optics and the sample when the x-ray radiation is emitted towards the sample,
   wherein the x-ray source is configured to emit x-ray radiation in the form of a fan beam, and
   wherein the x-ray source is configured to emit monochromatic x-ray radiation.

2. The X-ray imaging system of claim 1, wherein the primary detector is configured to determine an energy of detected x-ray photons.

3. The X-ray imaging system of claim 1, wherein the at least one secondary detector is configured to determine an energy of detected x-ray photons.

4. The X-ray imaging system of claim 1, wherein the at least one secondary detector comprises a plurality of secondary detectors.

5. The X-ray imaging system of claim 1, wherein the x-ray imaging system is configured to be movable around the sample.

6. The X-ray imaging system of claim 1, wherein the collimator is configured to allow only x-ray radiation scattered in a direction perpendicular to a direction of the x-ray radiation emitted by the x-ray source to reach the at least one secondary detector.

7. A method of x-ray imaging, the method comprising:
   emitting x-ray radiation from an x-ray source towards a sample;
   detecting x-ray radiation from the x-ray source passing through the sample with a primary detector positioned opposite the x-ray source, such that the x-ray source and the primary detector are disposed on opposite sides of the sample, respectively, when the x-ray radiation is emitted towards the sample;
   collimating x-ray radiation scattered in the sample with a collimator disposed between the sample and imaging optics when the x-ray radiation is emitted towards the sample;
   guiding the collimated x-ray radiation scattered in the sample onto a secondary detector with the imaging optics disposed between the secondary detector and the sample when the x-ray radiation is emitted towards the sample, and detecting the guided collimated x-ray radiation scattered in the sample with the secondary detector,
wherein x-ray radiation emitted by the x-ray source is emitted in the form of a fan beam passing through the sample, and
wherein the x-ray radiation emitted by the x-ray source is emitted as monochromatic x-ray radiation.

8. The method of claim 7, wherein photons detected by the primary detector that have lower energy than the monochromatic x-ray radiation emitted by the x-ray source are ignored for x-ray imaging.

9. The method of claim 8, wherein information relating to the photons detected by the primary detector that have lower energy than the monochromatic x-ray radiation emitted by the x-ray source is used for improving the x-ray imaging.

10. The method of claim 7, wherein intensity of the x-ray radiation detected by the secondary detector is used to analyze the sample.

11. The method of claim 7, wherein photons detected by the secondary detector that have lower energy than the monochromatic x-ray radiation emitted by the x-ray source are used to analyze the sample.

* * * * *